(12) United States Patent
Demond et al.

(10) Patent No.: US 8,486,105 B2
(45) Date of Patent: Jul. 16, 2013

(54) VASCULAR DEVICE FOR EMBOLI AND THROMBI REMOVAL AND METHODS OF USE

(75) Inventors: Jackson F. Demond, Santa Cruz, CA (US); Farhad Khosravi, San Mateo, CA (US); Jeff A. Krolik, Campbell, CA (US); Stephen Ramee, New Orleans, LA (US); Richard J. Renati, Los Gatos, CA (US); Amr Salahieh, Saratoga, CA (US); Kirk Hsueh-Kai Young, San Jose, CA (US)

(73) Assignee: Incept LLC, San Mateo, CA (US)

( * ) Notice: Subject to any disclaimer, the term of this patent is extended or adjusted under 35 U.S.C. 154(b) by 0 days.

(21) Appl. No.: 13/178,547

(22) Filed: Jul. 8, 2011

(65) Prior Publication Data
US 2011/0264135 A1    Oct. 27, 2011

Related U.S. Application Data

(63) Continuation of application No. 11/936,757, filed on Nov. 7, 2007, now Pat. No. 7,993,363, which is a continuation of application No. 10/103,022, filed on Mar. 21, 2002, now Pat. No. 7,306,618, which is a continuation-in-part of application No. 09/764,777, filed on Jan. 16, 2001, now abandoned, and a continuation-in-part of application No. 09/764,774, filed on Jan. 16, 2001, now abandoned, said application No. 09/764,777 is a continuation-in-part of application No. 09/470,681, filed on Dec. 23, 1999, now Pat. No. 6,203,561, said application No. 09/764,774 is a continuation-in-part of application No. 09/430,211, filed on Oct. 29, 1999, now Pat. No. 6,589,263, which is a continuation-in-part of application No. 09/364,064, filed on Jul. 30, 1999, now Pat. No. 6,530,939, said application No. 09/470,681 is a continuation-in-part of application No. 09/364,064, filed on Jul. 30, 1999, now Pat. No. 6,530,939.

(51) Int. Cl.
*A61M 29/00* (2006.01)

(52) U.S. Cl.
USPC .................................. 606/200; 604/164.05

(58) Field of Classification Search
USPC ............... 606/159, 194, 198, 200; 604/96.01, 604/104, 164.05
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |

(Continued)

*Primary Examiner* — Victor Nguyen
(74) *Attorney, Agent, or Firm* — Seager, Tufte & Wickhem LLC

(57) ABSTRACT

Apparatus and methods are provided for use in filtering emboli from a vessel and/or performing thrombectomy and embolectomy, wherein a vascular device disposed on a guidewire comprises a support hoop disposed from a suspension strut. Alternately, a support hoop having an articulation region may be directly connected to a region proximate the distal end of the guidewire. A blood permeable sac is affixed to the support hoop to form a mouth of the blood permeable sac. The support hoop is disposed obliquely relative to the longitudinal axis of the guidewire and is capable of being properly used in a wide range of vessel diameters. The vascular device collapses during removal to prevent material from escaping from the sac. A delivery sheath and introducer sheath for use with the vascular device of the present invention are also provided.

24 Claims, 13 Drawing Sheets

U.S. PATENT DOCUMENTS

| | | |
|---|---|---|
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |
| 4,969,891 A | 11/1990 | Gewertz |
| 5,011,488 A | 4/1991 | Ginsburg |
| 5,071,407 A | 12/1991 | Termin et al. |
| 5,133,733 A | 7/1992 | Rasmussen et al. |
| 5,160,342 A | 11/1992 | Reger et al. |
| 5,192,286 A * | 3/1993 | Phan et al. .................... 606/127 |
| 5,300,086 A | 4/1994 | Gory et al. |
| 5,324,304 A | 6/1994 | Rasmussen |
| 5,329,942 A | 7/1994 | Gunther et al. |
| 5,370,657 A | 12/1994 | Irie |
| 5,415,630 A | 5/1995 | Gory et al. |
| 5,419,774 A | 5/1995 | Willard et al. |
| 5,462,529 A | 10/1995 | Simpson et al. |
| 5,536,242 A | 7/1996 | Willard et al. |
| 5,549,626 A | 8/1996 | Miller et al. |
| 5,662,671 A | 9/1997 | Barbut et al. |
| 5,669,933 A | 9/1997 | Simon et al. |
| 5,713,917 A * | 2/1998 | Leonhardt et al. ............ 606/194 |
| 5,769,816 A | 6/1998 | Barbut et al. |
| 5,779,716 A | 7/1998 | Cano et al. |
| 5,800,457 A | 9/1998 | Gelbfish |
| 5,800,525 A | 9/1998 | Bachinski et al. |
| 5,807,398 A | 9/1998 | Shaknovich |
| 5,814,064 A | 9/1998 | Daniel et al. |
| 5,833,650 A | 11/1998 | Imran |
| 5,848,964 A | 12/1998 | Samuels |
| 5,911,734 A | 6/1999 | Tsugita et al. |
| 6,001,118 A * | 12/1999 | Daniel et al. .................. 606/200 |
| 6,066,149 A | 5/2000 | Samson et al. |
| 6,066,158 A | 5/2000 | Engelson et al. |
| 6,142,987 A | 11/2000 | Tsugita |
| 6,152,946 A | 11/2000 | Broome et al. |
| 6,168,579 B1 | 1/2001 | Tsugita |
| 6,171,327 B1 | 1/2001 | Daniel et al. |
| 6,203,561 B1 | 3/2001 | Ramee et al. |
| 6,206,868 B1 | 3/2001 | Parodi |
| 6,214,026 B1 * | 4/2001 | Lepak et al. .................. 606/200 |
| 6,221,006 B1 | 4/2001 | Dubrul et al. |
| 6,277,139 B1 | 8/2001 | Levinson et al. |
| 6,530,939 B1 | 3/2003 | Hopkins et al. |
| 6,589,263 B1 | 7/2003 | Hopkins et al. |
| 6,605,102 B1 | 8/2003 | Mazzocchi et al. |

* cited by examiner

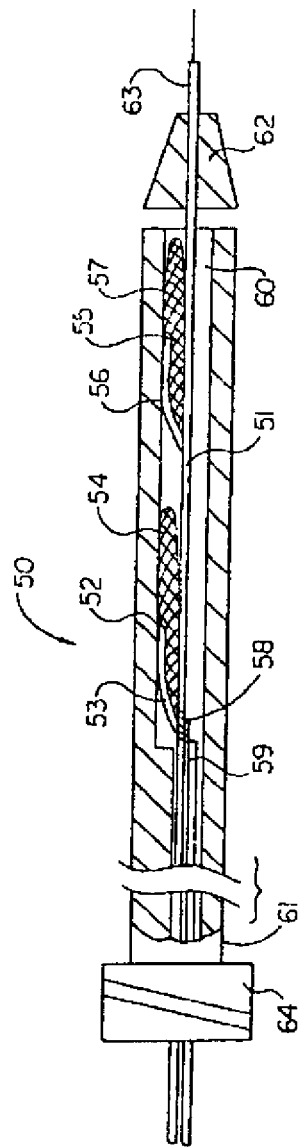
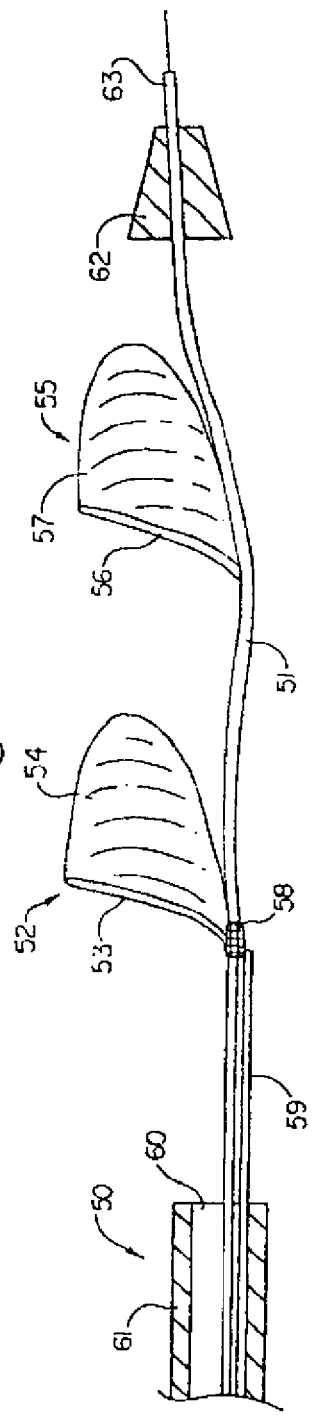
Fig.5A
Fig.5B

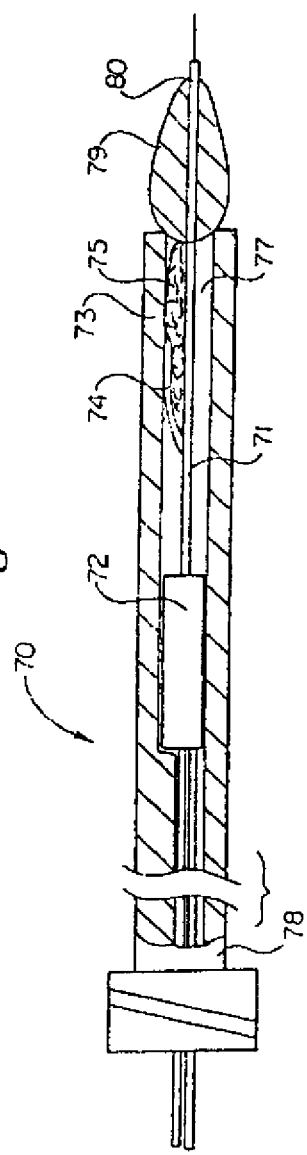
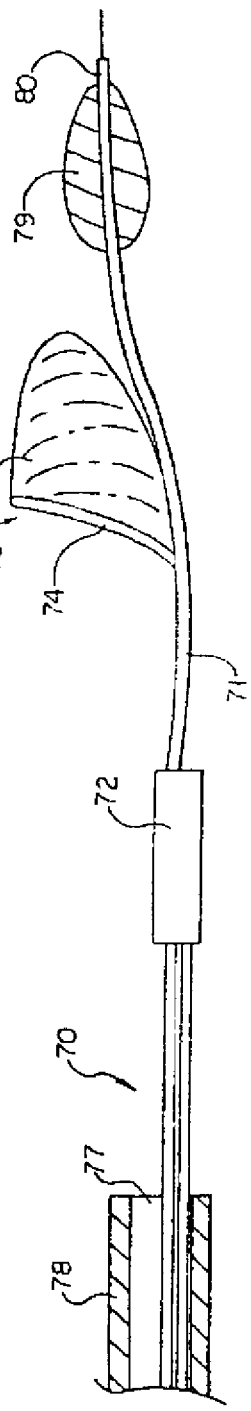

VASCULAR DEVICE FOR EMBOLI AND THROMBI REMOVAL AND METHODS OF USE

CROSS REFERENCES TO OTHER RELATED APPLICATIONS

This application is a continuation of application Ser. No. 11/936,757 filed Nov. 7, 2007, which is a continuation of application Ser. No. 10/103,022 filed Mar. 21, 2002, now U.S. Pat. No. 7,306,618, which is a continuation-in-part of application Ser. No. 09/764,777 filed on Jan. 16, 2001, now abandoned, and application Ser. No. 09/764,774 filed on Jan. 16, 2001, now abandoned; Ser. No. 09/764,777 is a continuation-in-part of Ser. No. 09/470,681 filed on Dec. 23, 1999, now U.S. Pat. No. 6,203,561; Ser. No. 09/764,774 is a continuation-in-part of Ser. No. 09/430,211 filed on Oct. 29, 1999, now U.S. Pat. No. 6,589,263; and Ser. No. 09/430,211 and Ser. No. 09/470,681 are both continuations-in-part of Ser. No. 09/364,064 filed on Jul. 30, 1999, now U.S. Pat. No. 6,530,939.

FIELD OF THE INVENTION

The present invention relates to apparatus and methods for filtering or removing matter from within a vascular system. More particularly, the present invention provides a low profile self-expanding vascular device useful for capturing emboli or foreign bodies generated during interventional procedures.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, also involves the introduction of foreign objects into the bloodstream, and also may result in the formation of clots or release of emboli. Such particulate matter, if released into the bloodstream, also may cause infarction or stroke.

Furthermore, interventional procedures may generate foreign bodies that are left within a patient's bloodstream, thereby endangering the life of the patient. Foreign bodies may include, for example, a broken guide wire, pieces of a stent, or pieces of a catheter.

Numerous previously known methods and apparatus have been proposed to reduce complications associated with embolism, release of thrombus, or foreign body material generation. U.S. Pat. No. 5,833,644 to Zadno-Azizi et al., for example, describes the use of a balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and an interventional devices, such as angioplasty balloon or stent delivery system, is advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage of radially expandable filter systems such as described in the foregoing patents is the relative complexity of the devices, which typically comprise numerous parts. Connecting more than a minimal number of such parts to a guide wire generally increases delivery complications. The ability of the guide wire to negotiate tortuous anatomy is reduced, and the profile of the device in its delivery configuration increases. Consequently, it may be difficult or impossible to use such devices in small diameter vessels, such as are commonly found in the carotid artery and cerebral vasculature. Moreover, such filter devices are generally incapable of preventing material from escaping from the filter during the process of collapsing the filter for removal.

Umbrella-type filter systems, such as described, for example, in U.S. Pat. No. 6,152,946 to Broome et al., also present additional drawbacks. One disadvantage of such systems is that the filters have only a limited range of operating sizes. Accordingly, a number of different filters of different sizes must be available to the clinician to treat different anatomies. Still further, such filters generally do not maintain apposition to the vessel wall when blood pressure pulses pass along a vessel, e.g., due to systole. In this case, because a blood pressure pulse can cause local swelling of the vessel diameter, the pressure pulse can cause the vessel to momentarily become lifted off the perimeter of the filter, thereby permitting emboli to bypass the filter.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member, so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, as compared to the umbrella-type filter elements described hereinabove, it too has drawbacks. One such drawback is that because the hoop is fixed directly to the guide wire, the cone-shaped basket may be unable to be fully deployed in a tortuous vessel. This problem is expected to arise, for example, where the resistance of the elongated member to bend to accommodate the tortuosity of the vessel causes the hoop and basket to be lifted away from the vessel wall, thereby providing a path for emboli-laden blood to bypass the filter.

In the aforementioned International Publication, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly, and is expected to result in a delivery profile too large to permit use of the device in critical regions of the body, such as the smaller coronary arteries, carotid arteries, and cerebral vasculature.

Due to the eccentric nature in the which the hoop is fastened to the elongated member in the foregoing International Application, it is expected that the perimeter of the hoop may be lifted away from the vessel wall which devices employing concentric lumens, e.g., angioplasty catheters or stent delivery systems, are brought into proximity with the filter.

Moreover, because the hoop in the aforementioned reference is directly fastened to the elongated member, there is also a risk that the basket will collapse or become wound around the elongated member due to twisting of the elongated member, e.g., during transluminal insertion of the filter, or during manipulation of the proximal end of the elongated member during insertion or withdrawal of interventional devices along the elongated member.

In view of the foregoing disadvantages of previously known apparatus and methods, it would be desirable to provide a vascular device, e.g., for use as a vascular filter, that overcomes such disadvantages and employs few components.

It also would be desirable to provide a vascular device for removing thrombus from a vascular system that overcomes the disadvantages of previously known thrombectomy devices.

It also would be desirable to provide a vascular device that is capable of being contracted to a small delivery profile, thus permitting use of the device in small vessels.

It further would be desirable to provide a vascular device that is capable of being contracted to a sufficiently small profile that it may be retrieved using the guide wire lumen of previously known treatment devices, and without the need for specialized delivery catheters.

It still further would be desirable to provide a vascular device that reduces the risk of emboli from escaping from the device when the device is collapsed and removed.

It also would be desirable to provide a reliable vascular filter that is capable of being fully deployed in tortuous anatomy.

It also would be desirable to provide a vascular filter that is resistant to becoming disengaged from the vessel wall due to lateral movements of the guide wire to which the vascular filter is coupled.

It further would be desirable to provide a vascular filter that is capable of spanning a range of vessel sizes, thereby reducing inventory requirements.

It also would be desirable to provide a vascular filter that is resistant to becoming disengaged from the vessel wall due to local swelling of the vessel diameter as blood pressure pulses along the vessel past the filter deployment location.

It further would be desirable to provide a vascular filter that is resistant to collapse or disengagement from the vessel wall due to torsional forces applied to the guide wire to which the vascular filter is coupled.

It still further would be desirable to provide a vascular device that is capable of being contracted to a small delivery profile, thus permitting use of the device in small vessels.

SUMMARY OF THE INVENTION

In view of the foregoing, it is an object of the present invention to provide a vascular filter that overcomes disadvantages of previously known vascular filters, thrombectomy/embolectomy and foreign body removal devices, and employs few components.

It also is an object of this invention to provide a vascular device that is capable of being contracted to a small delivery profile, thus permitting use of the device in small vessels.

It is a further object of the present invention to provide a vascular device that is capable of being contracted to a sufficiently small profile that it may be retrieved using the guide wire lumen of previously known treatment devices, and without the need for specialized delivery catheters.

It is another object of this invention to provide a vascular device that reduces the risk of emboli or thrombus removed from the vessel wall escaping from the device when the device is collapsed and removed.

It is another object of the present invention to provide a reliable vascular filter that is capable of being fully deployed in tortuous anatomy.

It is also an object of the present invention to provide a vascular filter that is resistant to becoming disengaged from the vessel wall due to lateral movements of the guide wire to which the vascular filter is coupled.

It is another object of this invention to provide a vascular filter that is capable of spanning a range of vessel sizes, thereby reducing inventory requirements.

It is a further object of the present invention to provide a vascular filter that is resistant to becoming disengaged from the vessel wall due to local swelling of the vessel diameter as blood pressure pulses along the vessel past the filter deployment location.

It is another object of the present invention to provide a vascular filter that is resistant to collapse or disengagement from the vessel wall due to torsional forces applied to the guide wire to which the vascular filter is coupled.

It is a further object of the present invention to provide a vascular device that is capable of being contracted to a small delivery profile, thus permitting use of the device in small vessels.

These and other objects of the present invention are accomplished by providing a vascular device, suitable for use as a vascular filter or thrombectomy/embolectomy device, that comprises a blood permeable sac affixed at its perimeter to a support hoop. In accordance with the principles of the present invention, the support hoop, having an articulation region, is attached to a distal region of an elongated member, such as a guide wire, via a suspension arrangement which permits the guide wire to rotate and move laterally relative to the support hoop, without the support hoop becoming disengaged from the vessel wall. The support hoop supports a proximally-oriented mouth of the sac when the device is deployed in a vessel. The device also may comprise a nose cone to facilitate percutaneous introduction, and a delivery sheath having one or more lumens. The lumens may further be configured for a rapid exchange mode of introduction along the guide wire.

In a first embodiment, the support hoop includes one or more reduced-thickness articulation regions that enable the support hoop to be contracted to very small radii of curvature without the problems of increased stiffness and kinking of previously known devices. In an alternative embodiment, the articulation region may comprise a gap in the support hoop bridged by the perimeter of the blood permeable sac. In another embodiment, the articulation region may comprise a gap in the support hoop bridged by a biocompatible polymer.

The support hoop preferably also has a curved profile that prevents the articulation region, when folded, from damaging the wall of the vessel. The curved profile permits the device to effectively contact the walls of the vessel and reduce emboli or thrombus removed from the vessel wall from bypassing the sac. Moreover, the articulation region, when combined with a support hoop having a curved profile, causes the sides of the support hoop to fold inwards towards one-another when the vascular device is collapsed into a sheath for removal. This, in turn, closes the mouth of the sac and reduces the potential for emboli or thrombus to be released from the vascular device during removal.

Advantageously, use of an articulation region permits vascular devices of the present invention to be contracted to very small diameters, thereby enabling the use of delivery catheters having diameters as small as 2.5 Fr. Moreover, the vascular devices may be retracted within the guide wire lumens of conventional treatment devices, such as angioplasty catheters and stent delivery systems, thereby obviating the need to re-insert a specialized delivery catheter to remove the vascular device. However, a retrieval sheath having a distal region that flares or expands outwardly to receive the emboli-filled sac upon completion of an interventional procedure, and which reduces risk of rupture to the sac, optionally may be provided in accordance with the present invention.

In thrombectomy applications, the vascular device may include a thrombectomy element comprising a blood permeable sac and support hoop as described above. The thrombectomy element may be attached to the elongated member proximal of the vascular filter or may comprise a separate catheter. In a preferred embodiment, the thrombectomy element is similar in construction to the vascular filter and may be retracted independently. Alternatively, the thrombectomy element may be any conventional atherectomy device used in conjunction with the vascular filter and may be advanced and retracted either in conjunction or independently of the vascular filter.

In another embodiment, the suspension arrangement includes a support tube disposed concentrically over the guide wire that permits the guide wire to rotate relative to the support tube without transmitting torsional forces to the filter. In addition, the support hoop includes a linear or curved flexible strut that holds the support in at a near concentric position relative to the guide wire, thereby providing the large lateral deflections of the guide wire without the guide wire contacting the support hoop.

In alternative embodiments, the suspension arrangement may further comprise additional coils formed in the flexible strut to enhance apposition of the support hoop to the vessel walls, or a nose cone mounted on the support tube. As a further alternative, the suspension arrangement may be configured as series of loops or coil turns in the guide wire proximal to the point of attachment of the support hoop, thereby isolating the filter from lateral or torsional disturbances to the proximal end of the guide wire.

A single use delivery sheath and introducer sheath suitable for use with the vascular filter of the present invention are also provided, as are methods of using embodiments of the present invention.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5A and 5B are, respectively, side-sectional views depicting a vascular device, including a thrombectomy element, disposed within a delivery sheath, and in a deployed state;

FIGS. 7A and 7B are, respectively, side-sectional views depicting an alternative embodiment of the vascular device of FIG. 5 disposed within a delivery sheath, and in the deployed state;

FIGS. 18A-18C are detailed views of the suspension arrangement and nose cone construction of the embodiment of FIG. 15, while FIG. 18C is a end view of the vascular filter taken along view line C-C of FIG. 18A;

DETAILED DESCRIPTION OF THE INVENTION

Figure 1A:
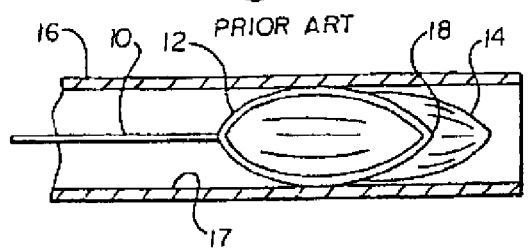
FIGS. 1A and 1B are, respectively, a side-sectional view of a previously known vascular device contracted within a delivery sheath, and an end view of that vascular device deployed in a vessel.
Figure 1B:
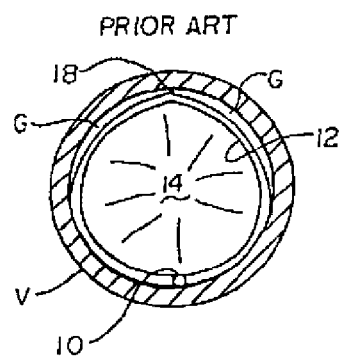

Referring to FIGS. 1A and 1B, some of the disadvantages associated with previously known vascular devices, such as the emboli filters described in the above-mentioned International Publication WO 98/39053, are described. In FIG. 1, the vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of vessel V.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.035" or smaller are used, a hoop of nitinol or multi-strand nitinol cable having a diameter of 0.0055" will form kink 18. Kink 18 in turn may apply relatively high localized pressure and friction against wall 17 of sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability of the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular device of the present invention solves the above-described disadvantages, providing a vascular device, suitable for use as a vascular filter or thrombectomy/embolectomy device, with a self-expanding support hoop that is sufficiently thick to radially expand and urge a blood permeable sac into engagement with the vessel wall, but which includes an articulation region that overcomes the problems associated with kinking. In particular, the vascular device of the present invention includes a reduced thickness articulation region and a preformed curved profile that avoids the difficulties of previously known systems while providing a high degree of efficacy in capturing emboli or thrombus, and ease of deployment and retrieval.

Figure 2A:
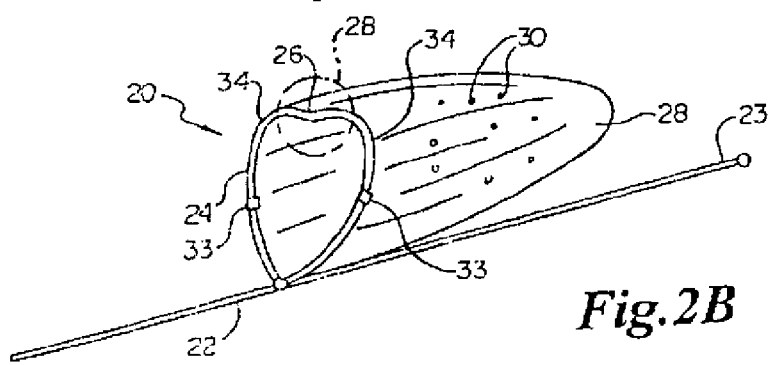
FIGS. 2A and 2B are, respectively, a perspective view of a vascular device constructed in accordance with the principles of the present invention in a deployed state, and a detailed view of the articulation region of the device of FIG. 2A.
Figure 2B:
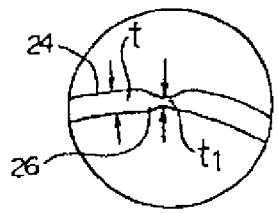

Referring now to FIGS. 2A and 2B, vascular device 20 constructed in accordance with the principles of the present invention comprises guide wire 22, support hoop 24 having articulation region 26, and blood permeable sac 28 affixed to support hoop 24. Sac 28 is coupled to support hoop 24 so that the support hoop 24 forms an opening for the sac. Support hoop 24 preferably is connected to guide wire 22 near distal end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof. The material should be sufficiently thin, such that the sac is non-thrombogenic. Sac 28 includes openings or pores 30 that permit blood cells to pass through the sac substantially unhindered, while capturing any larger emboli, thrombus, or foreign bodies that may be released during a procedure, such as angioplasty or stent placement. In a preferred embodiment, sac 28 has openings or pores 30 in a range of about 20 to 400 microns in diameter, and more preferably, about approximately 80 microns. These pore sizes permit red blood cells (which have a diameter of approximately 5 microns) to easily pass through the sac, while capturing thrombus or emboli.

Pores 30 are preferably formed by a laser drilling process. For example, a thin sheet of the flexible biocompatible material may be thermoformed to create sac 28, for example, by stretching the sheet over a mandrel, by dip forming, or by blow molding. Sac 28 may alternatively be fabricated from an extruded tube of the biocompatible material. A flat metal mask, with tiny holes approximately the size of pores 30, may then be placed in front of the sac. A laser having a beam diameter equal to or greater than the diameter of the material illuminates the mask. The laser beam passes through the holes in the mask and strikes the material, thereby forming pores 30 in sac 28.

Laser drilling may also be accomplished with a laser having a beam diameter approximately the size of pores 30, in which case pores 30 may drilled individually. Sac 28 may alternatively comprise a woven material, for example, formed from the above-mentioned polymers, having a pore diameter determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular device 20, described hereinafter, support hoop 24 folds in half and collapses to fit within a small diameter delivery sheath. When vascular device 20 is in a deployed state, as depicted in FIG. 2A, support hoop 24 resumes its preformed shape.

Support hoop 24 preferably comprises nitinol wire, although it may also be formed from a multi-strand nitinol cable, a spring tempered stainless steel, or other super-elastic material.

In accordance with the principles of the present invention, support hoop 24 includes one or more reduced-thickness articulation regions 26, and preformed curved regions 34. As depicted in FIG. 2B, articulation region 26 includes a region having reduced thickness t, compared to thickness t of the remainder of support hoop 24. Articulation region 26 and curved regions 34 enable support hoop 24 to fold with a pre-determined shape when vascular device 20 is collapsed to a contracted state for delivery or retrieval.

In FIG. 2B, articulation region 26 is depicted as a localized reduction in the thickness of support hoop 24, as may be achieved, for example, using conventional grinding, chemical etching, or electroless polishing processes. Alternatively, support hoop 24 may be continuously tapered along its circumference, so that articulation region 26 results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In a preferred embodiment of vascular device 20 of the present invention, vascular device 20 easily fits within a delivery sheath having an inner diameter of 0.033", and, more preferably, may be used with a delivery sheath having an inner diameter as small as 0.026". The deployed diameter of support hoop 24 preferably is approximately 7 mm, while guide wire 22 preferably has a diameter of 0.014". The distal end of guide wire 22 also may be tipped with a spring section or coil tip, as is per se known.

Support hoop 24 preferably is constructed of 0.0055" nitinol wire tapered (by a grinding, chemical etching, or electroless polishing process) to 0.0025" at articulation region 26. Specifically, articulation region 26 preferably consists of a length about 0.05" long and having a diameter of 0.0025", coupled on either side to curved regions 34. Each of curved regions 34 includes a length of wire that is tapered from a diameter of 0.055" to a diameter of 0.0025" over a length of about 0.025". Support hoop 24 also may include radiopaque features, such as gold or platinum bands 33, spaced at intervals around the circumference of support hoop 24, or a coil of radiopaque material wrapped around the support hoop, or a gold plated coating.

Figure 3:
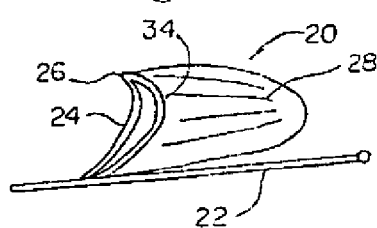
FIG. 3 is a perspective view of the vascular device of FIG. 2 in a folded configuration, prior to removal.
Figure 4:
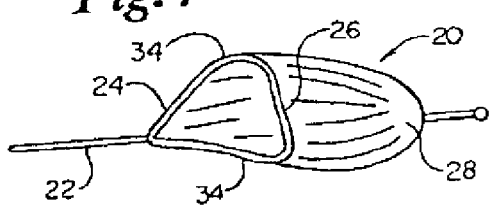
FIG. 4 is a plan view of the vascular device of FIG. 2.

Referring to FIGS. 3 and 4, additional features of vascular device 20 are described. FIG. 3 depicts vascular device 20 of FIG. 2A in a contracted state, while FIG. 4 illustrates a directional change in support hoop 24 preferably caused by the presence of curved regions 34. Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac than would otherwise be possible, without increasing the risk of material escaping from the device when the sac is collapsed for retrieval. Use of a smaller or shallower sac also enables vascular device 20 to be delivered in a smaller delivery sheath, having an inner diameter as small as 0.026" for the preferred embodiment.

Vascular devices of the present invention also may comprise a thrombectomy element constructed similarly to vascular filter 20 described above. Alternatively, vascular filter 20 may be used in conjunction with the thrombectomy element. In such embodiments, the thrombectomy element preferably is coupled to the elongated member proximal of the vascular filter, or may comprise a separate catheter. In a preferred embodiment, the thrombectomy element is similar in construction to filter 20, and may be retracted independently. Alternatively, the thrombectomy element may be any conventional atherectomy device used in conjunction with the vascular filter and may be advanced and retracted either in conjunction with, or independently of, the vascular filter.

Referring now to FIGS. 5A and 5B, an illustrative embodiment of a vascular device of the present invention including a thrombectomy element is described. Vascular device 50 comprises guide wire 51, thrombectomy element 52 including support hoop 53 and blood permeable sac 54, and vascular filter 55 including support hoop 56 and blood permeable sac 57. Filter hoop 56 is attached to guide wire 51 while thrombectomy hoop 53 is attached to ring 58. Ring 58 is attached to pull wire 59 and has a bore through which guide wire 51 passes. Ring 58 therefore acts as a linear bearing and allows thrombectomy hoop 53 to be moved by pull wire 59 independently of guide wire 51. Alternatively, thrombectomy element 52 may omit sac 54 and simply comprise a wire hoop; in this case severed thrombus is captured by vascular filter 55.

In FIG. 5A, support hoops 53 and 56 and blood permeable sacs 54 and 57 are contracted to a delivery state within lumen 60 of delivery sheath 61. Delivery sheath 61 includes nose cone 62 affixed to distal region 63 of guide wire 51. In FIG. 5B, vascular device 50 is shown deployed in a vessel. As illustrated in FIG. 5B, vascular filter 55 expands to engage the perimeter of the vessel and prevent thrombus from bypassing the blood permeable sac, while thrombectomy element 52 engages the vessel wall proximal of vascular filter 55. As described hereinbelow, proximal movement of thrombectomy device 52 scrapes thrombus from the wall of the vessel when pull wire 59 pulls ring 58 and support hoop 53 proximally.

Figure 6A:
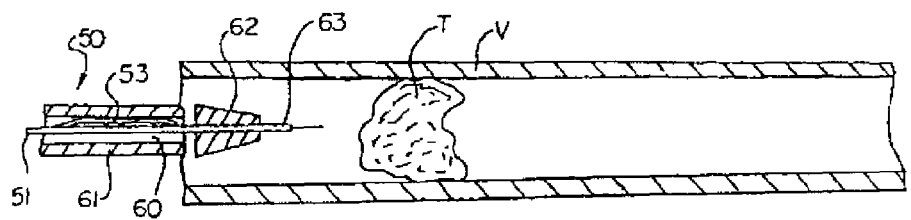
FIGS. 6A-6E are side-sectional views depicting a method of deploying, using and retrieving the vascular device of FIG. 5.

Referring now to FIGS. 6A-6E, an illustrative method of using the vascular device of FIG. 5 for thrombectomy is described. In FIG. 6A, guide wire 51 is manipulated into position proximal to thrombus T within vessel V using well-known percutaneous techniques. Vascular device 50 of FIGS. 5A and 5B is disposed in its contracted delivery state within the distal end of delivery sheath 61 and the delivery sheath is advanced through the vessel using distal end 63 of guide wire 51. The sides of support hoops 53 and 56 are folded together and become elongated when drawn within delivery sheath 61, as described with respect to vascular device 20 of FIGS. 2-4.

Figure 6B:
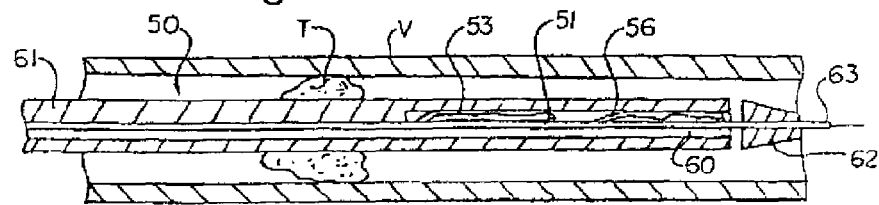

With respect to FIG. 6B, once delivery sheath 61 is disposed at the desired location proximal to thrombus T within a patient's vessel V, such as a coronary artery or carotid artery, for example, based on the position of, for example, radiopaque bands under a fluoroscope, vascular device 50 is advanced through thrombus T. Distal end 63 of guide wire 51 is advanced through the lesion, then nose cone 62 gradually increases the diameter of the void within thrombus T so that the remainder of delivery sheath 61 can be advanced far enough that thrombectomy element 52 (still within delivery sheath 61) is located distal to thrombus T.

Figure 6C:
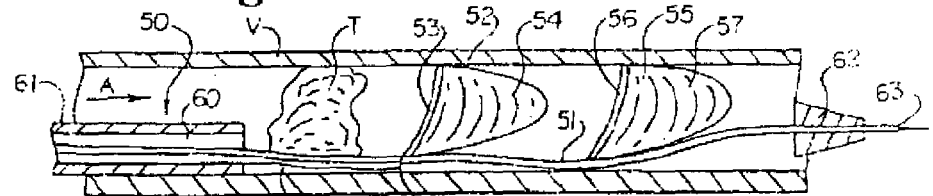

With vascular device 50 in position, guide wire 51 is held stationary while delivery sheath 61 is retracted proximally, as seen in FIG. 6C. Alternatively, delivery sheath 61 may be held stationary while guide wire 51 is advanced. In either case, when vascular device 50 is no longer confined within delivery sheath 61, support hoops 53 and 56 expand to seal against the walls of the vessel V and deploy blood permeable sacs 54 and 57, respectively. Blood continues to flow through vessel V in direction A, impeded only by thrombus T.

Figure 6D:
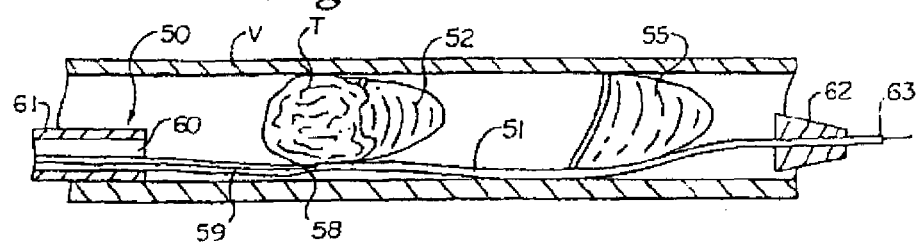

In FIG. 6D, once vascular device 50 is deployed in vessel V, thrombus T is removed in the following manner. Vascular filter support hoop 53 is rigidly attached to guide wire 51, while thrombectomy support hoop 53 is attached to pull wire 59 via ring 58. Thrombectomy element 52 then is retracted proximally to scrape along the wall of the vessel V by motion at the proximal end of pull wire 59. Thrombus T, located proximal to thrombectomy element 52, is excised so that it is captured in blood permeable sac 54 during the retraction.

Figure 6E:
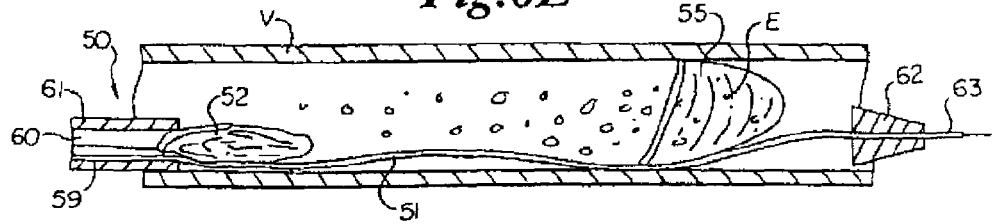

With respect to FIG. 6E, once thrombus T has been captured within sac 54, pull wire 59 is pulled proximally to cause the sides of thrombectomy support hoop 53 to collapse together to close the mouth of sac 28 (see FIG. 3). Additional proximal retraction of pull wire 59 causes support hoop 53 and sac 54 to enter within lumen 60 of delivery sheath 61, restoring normal blood flow to vessel V. Meanwhile, vascular filter 55 is in a position distal to thrombectomy element 52 to trap emboli E, i.e., pieces of plaque dislodged from either thrombus T or the walls of vessel V by thrombectomy element 52. Once any emboli E have been collected, filter hoop 56 and sac 57 are retracted into delivery sheath 61 by motion at the proximal end of guide wire 51, in a manner similar to the retraction of hoop 53 and sac 54. Once guide wire 51 has been fully retracted and nose cone 62 at the distal end 63 of guide wire 51 is again in contact with delivery sheath 61, the delivery sheath is withdrawn with vascular device 50, the trapped thrombus T and any trapped emboli E.

Advantageously, the compliant design of vascular device 50 permits the device to be contracted to its delivery state within the guide wire lumen of conventional previously known interventional devices. Accordingly, unlike previously known vascular devices, which require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

Referring now to FIGS. 7A and 7B, an alternative embodiment of the vascular device of FIG. 5 is described. Vascular device 70 comprises guide wire 71, thrombectomy element 72 and vascular filter 73 including support hoop 74 and blood permeable sac 75. Filter hoop 74 is attached to guide wire 71, while thrombectomy element 72 is disposed to slide along guide wire 71. Alternatively, thrombectomy element 72 may be disposed on a separate catheter element that extends either through lumen 77 of delivery sheath 78 or is separately disposed proximal of vascular filter 73.

FIG. 7A shows thrombectomy element 72 and vascular filter 73 contracted in a delivery state within lumen 77 of delivery sheath 78. Delivery sheath 78 includes nose cone 79 affixed to distal region 80 of guide wire 71. In FIG. 7B, vascular device 70 is shown in the deployed state. Thrombectomy element 72 may comprise any of a family of known thrombectomy, atherectomy, or, alternatively, drug delivery devices suitable for use in conjunction with device 73.

Specifically, thrombectomy element 72 may comprise any of: a rotary ablation device, such as described in U.S. Pat. No. 4,867,156 to Stack et al., U.S. Pat. No. 4,990,134 to Auth, and U.S. Pat. No. 5,314,407 to Auth et al.; an atherectomy technology, such as described in U.S. Pat. No. 5,181,920 to Mueller et al., and U.S. Pat. No. 5,074,841 to Ademovic et al.; or a balloon embolectomy technology, such as described in U.S. Pat. No. 3,923,065 to Nozick et al., U.S. Pat. No. 5,769,871 to Mers Kelly et al., U.S. Pat. No. 5,192,290 to Hilal, U.S. Pat. No. 5,112,347 to Taheri, and U.S. Pat. No. 4,030,503 to Clark III. All of the foregoing patents are incorporated herein by reference. Thrombectomy element 72 alternatively may comprise a wire loop or ring such as alternatively described for the embodiment of FIGS. 5A and 5B, a laser ablation device, a chemical flushing system, etc.

Figure 8A:
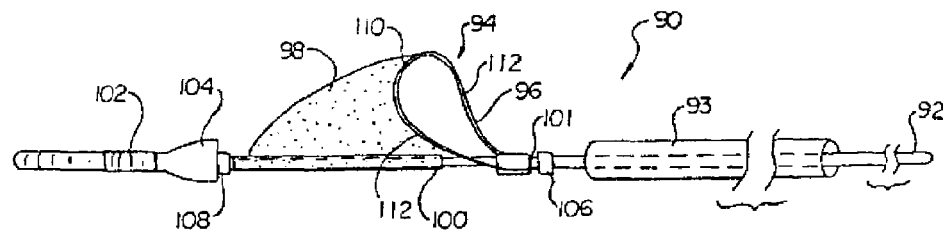
FIGS. 8A and 8B are views depicting another alternative embodiment of the present invention having multiple articulation regions and shown, respectively, in side-view in the deployed state and in side-view, partially in section, disposed within a delivery sheath.
Figure 8B:
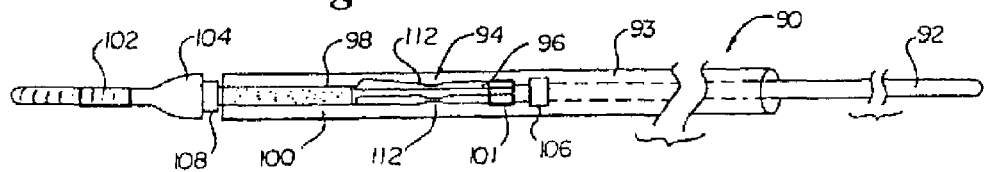

With reference to FIGS. 8A and 8B, another alternative embodiment of the present invention is described wherein the vascular filter element includes multiple articulation regions. Vascular device 90 comprises guide wire 92, sheath 93, and filter 94 comprising 15 support hoop 96, blood permeable sac 98, spinner tube 100, and bearing 101. Sac 98 is attached along its length to spinner tube 100, which is coaxially and slidably disposed about guide wire 92. Support hoop 96 is attached to bearing 101, which is also coaxially and slidably disposed about guide wire 92. Guide wire 92 comprises floppy distal end 102, nose cone 104, proximal stop 106, and distal stop 108. Filter 94 is disposed between the proximal and distal stops.

Support hoop 96 is similar to support hoop 24 of FIG. 2A, except that it includes multiple articulation regions. Closure articulation region 110 facilitates collapse of filter 94 to the delivery configuration of FIG. 8B within sheath 93, while tracking articulation regions 112 act as bend points for easy tracking in tortuous anatomy. Tracking articulation regions 112 beneficially allow vascular device 90 to be used in a wider variety of applications, including neurothrombectomy applications.

Figure 9:
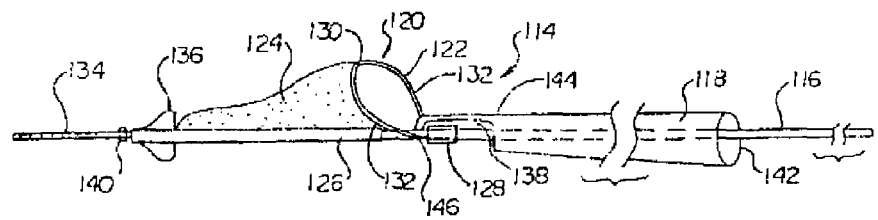
FIG. 9 is a side-view of an alternative embodiment of the vascular device of FIG. 8 comprising a positive locking feature.

Referring to FIG. 9, yet another alternative embodiment of the present invention having a positive locking feature is described. Vascular device 114 comprises guide wire 116, sheath 118, and filter 120 including support hoop 122, blood permeable sac 124, spinner tube 126, and bearing 128. Sac 124 is attached along its length to spinner tube 126, while support hoop 122 is attached to bearing 128. Both spinner tube 126 and bearing 128 are coaxially and slidably disposed about guide wire 116. Spinner tube 126 comprises nose cone 136, thereby allowing rotation of guide wire 116 without rotation of the larger diameter nose cone. Support hoop 122 comprises articulation region 130 disposed between curved regions 132. Guide wire 116 comprises floppy distal end 134, proximal stop 138, and distal stop 140, any of which may be radiopaque to facilitate positioning within a vessel. Filter 120 is disposed between the proximal and distal stops.

Sheath 118 comprises lumen 142, in which filter 120 is disposed in a collapsed configuration during delivery and retrieval Sheath 118 further comprises locking distal end 144 having wedge 146. During deployment, sheath 118 is retracted with respect to filter 120 to allow support hoop 122 to expand and sealingly engage a patient's vessel. Further retraction of sheath 118 causes wedge 146 of distal end 144 to lodge between opposing curved regions 132 of support hoop 122, there by inhibiting articulation of articulation region 130 and "locking" hoop 122 in the deployed configuration.

When used as thrombectomy elements in a dual arrangement as depicted in FIG. 5, the support hoops of the present invention may have a tendency to close as they are retracted through thrombus in the manner seen, for example, in FIG. 6D. Referring again to FIG. 9, locking hoop 122 in the deployed configuration allows the hoop to be retracted through thrombus without closing the mouth of the hoop. Once thrombus has been captured in blood permeable sac 124, sheath 118 may be advanced with respect to hoop 122 in order to remove wedge 146 from between curved regions 132 of the support hoop, thereby "unlocking" the support hoop. Further advancement of sheath 118 with respect to hoop 122 causes filter 120 to articulate at articulation region 130 and collapse for retrieval within lumen 142 of sheath 118.

Figure 10:
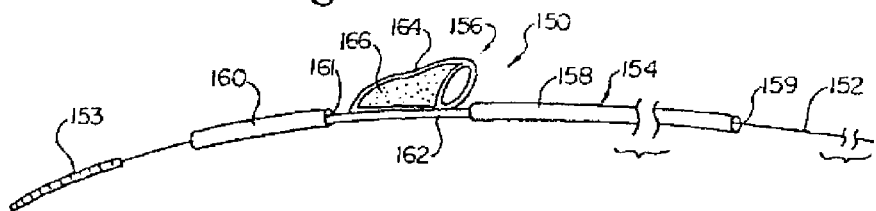
FIG. 10 is a side-view depicting yet another alternative embodiment of the vascular device of the present invention having a filter frame.

Referring to FIG. 10, a still further alternative embodiment of the present invention having a filter frame is described. As with vascular device 114 of FIG. 9, vascular device 150 of FIG. 10 addresses the potential for support hoops of the present invention to close as they are retracted through thrombus. Vascular device 150 comprises guide wire 152 having floppy distal end 153, sheath 154, and filter 156.

Sheath 154 comprises proximal section 158 having lumen 159, distal section 160 having lumen 161, and bridge section 162 disposed therebetween. Bridge section 162 may be a portion of proximal section 158 or of distal section 160 that has been cut away to provide a window through which filter 156 may expand. Alternatively, bridge section 162 may comprise a rod that connects the proximal section to the distal section.

Filter 156 comprises filter frame 164, and blood permeable sac 166 attached thereto. Frame 164 is attached to guide wire 152 and is described in greater detail with respect to FIGS. 11A-11D. In use, filter 156 is disposed in a collapsed configuration during delivery within distal section 160 of sheath 154. Filter 156 then is expanded to the deployed configuration by retracting element 156 with respect to sheath 154 until the filter is disposed in bridge section 162 of the sheath. Frame 164 dynamically expands to the deployed configuration of FIG. 10. Vascular device 150 is then proximally retracted to draw filter 156 through thrombus and capture the thrombus in sac 166.

Referring now to FIGS. 11A-11D, in conjunction with FIG. 10, filter frame 164 is described in greater detail. Frame 164 comprises support hoop 168 having reduced-thickness articulation region 170 disposed between curved regions 172. Hoop 168 is coupled to arch support 174. Arch support 174 comprises hinge articulation region 176 disposed between first and second support struts 178 and 180, respectively. First strut 178 is coupled to articulation region 170, while second strut 180 is coupled to curved regions 172. Hinge section 176 and articulation region 170 are preferably formed of a superelastic material, for example, a nickel titanium alloy (nitinol) or spring tempered stainless steel. Guide wire 152 of FIG. 10 is preferably connected to first support strut 178, thereby providing filter frame 164 with the "proximal tilt" seen in FIG. 10.

When retracted through thrombus, arch support 174 provides structural stability that maintains frame 164 in the deployed configuration. Frame 164 may then be collapsed back to the delivery configuration by impinging distal section 160 of sheath 154 against hinge articulation 176. The hinge articulation deforms and advances second strut 180 with respect to first strut 178, thereby causing support hoop 168 to deform at articulation region 170 and collapse for retrieval within distal section 160.

In addition to its ability to maintain support hoop 168 in the deployed configuration, filter frame 164 provides blood permeable sac 166 with increased strength against breaking. It also prevents camming or stiction and allows easy movement back and forth of filter 156 within a patient's vessel without damaging the vessel walls.

Figure 12:
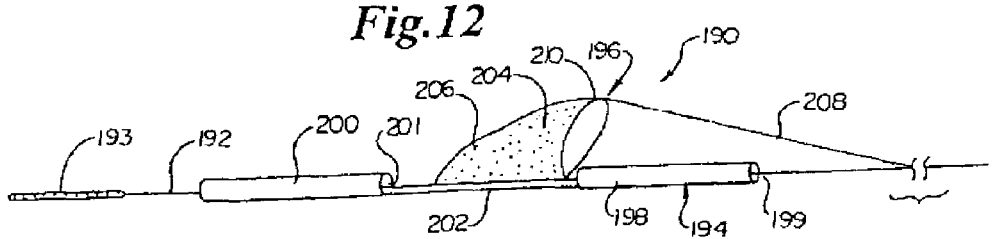
FIG. 12 is a side-view of an alternative embodiment of the vascular device of FIG. 10 having a tension thread.
Figure 11A:
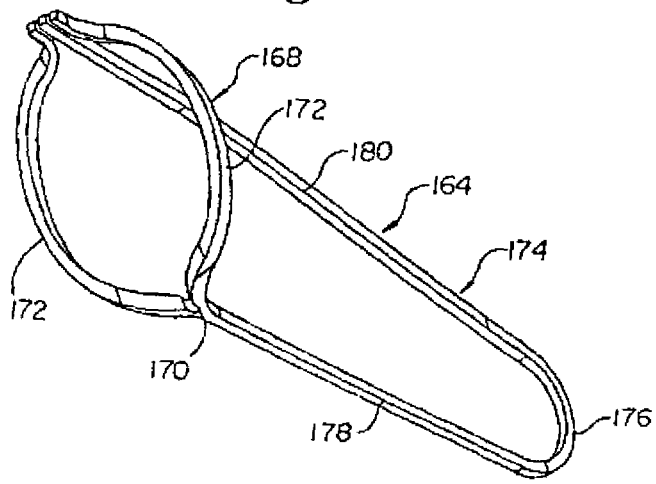
FIGS. 11A-11D are, respectively, isometric, bottom, side, and front views of the filter frame of FIG. 10.
Figure 11B:
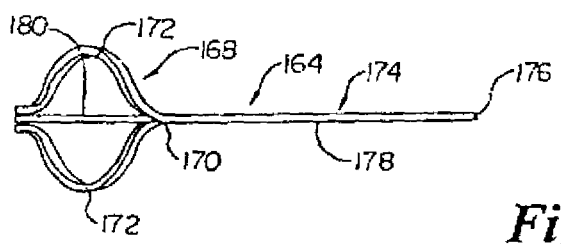
Figure 11C:
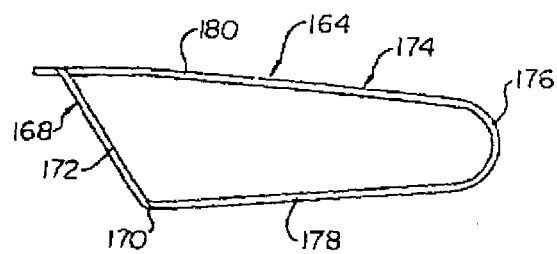
Figure 11D:
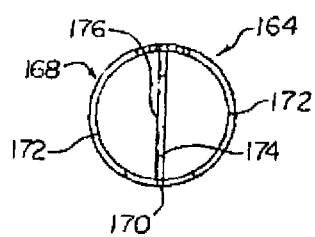

With reference to FIG. 12, an alternative embodiment of the vascular device of FIG. 10 having a tension thread is described. Vascular device 190 comprises guide wire 192 having floppy distal end 193, sheath 194, and filter 196. Sheath 194 is similar to sheath 154 of FIG. 10 and comprises proximal section 198 having lumen 199, distal section 200 having lumen 201, and bridge section 202 disposed therebetween. Filter 196 comprises support hoop 204, blood permeable sac 206, and tension thread 208. Support hoop 204 is attached to guide wire 192. Likewise, sac 206 is attached to the guide wire along its length, and is also attached to support hoop 204. Support hoop 204 comprises articulation region 210 that allows support hoop 204 to collapse to the delivery configuration via sheathing from the distal side of the hoop.

Tension thread 208 is connected to support hoop 204 near articulation region 210, and is connected to guide wire 192 proximal of hoop 204. Thread 208 is dimensioned such that the thread is taut when hoop 204 is in the expanded deployed configuration of FIG. 12. When support hoop 204 is disposed in the delivery configuration within distal section 200 of sheath 194, the distance between where tension thread 208 is connected to support hoop 204 and where the tension thread is connected to guide wire 192 is shorter than when support hoop 204 is in the deployed configuration. Thus, tension thread 208 is lax in the delivery configuration. This is made possible by distal sheathing of filter 196.

When used in a thrombectomy application, such as the dual arrangement of FIG. 5, filter 196 is expanded to the deployed configuration, and vascular device 190 is retracted proximally through thrombus. Taut tension thread 208 ensures that articulation region 210 does not articulate and that the mouth of support hoop 204 remains open while thrombus is captured in blood permeable sac 206.

Figure 13A:
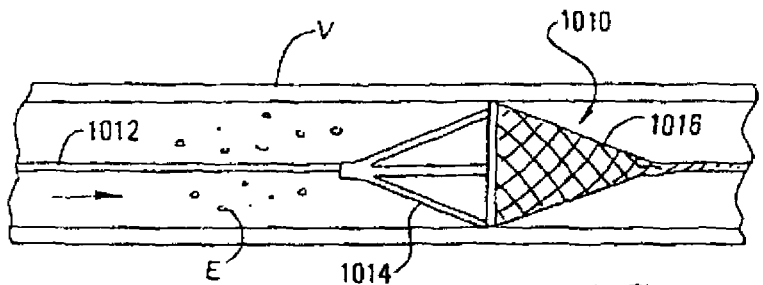
FIGS. 13A-13C are, respectively, side and ends view of an illustrative previously known vascular filter shown deployed in a straight length of vessel.

Referring to FIGS. 13A-13C and 14, some of the disadvantages of previously known umbrella-type filters are described as context for the benefits achievable with the vascular filter of the present invention. FIG. 13A shows a previously known umbrella-type filter 1010 deployed in a straight length of vessel V, with emboli E approaching with antegrade flow. Filter 1010 is disposed on guidewire 1012 and includes radially-extending struts 1014 that support biocompatible mesh 1016.

Figure 13B:
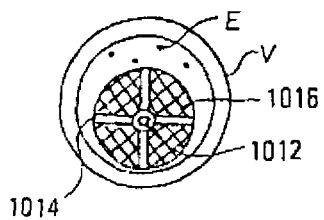

FIG. 13B illustrates a situation that may arise wherein the clinician underestimates the diameter of vessel V and deploys an undersized vascular filter 1010. Because umbrella type filters generally are capable of spanning only a narrow range of vessel diameters, the result as depicted in FIG. 13B may obtain where filter 1010 is undersized for the vessel diameter. In this case, emboli E will bypass around the edges of the filter 1010. Where umbrella-type filters of the kind depicted in FIG. 13 are used, the clinician must therefore exercise great care in selecting the appropriate filter size, and the hospital must carry a range of sizes to fit different patient anatomies.

Moreover, even where the clinician has selected a vascular filter appropriate for the nominal diameter of vessel V, bypass of emboli may still arise. This may occur, for example, where the vessel is subject to localized swelling as blood vessel pulses, e.g., during systole, pass along the length of the vessel. In this case, which has been observed to occur, for example, in the carotid arteries, the vessel wall may be momentarily lifted away from the perimeter of the vascular filter 1010, permitting a bypass situation similar to that depicted in FIG. 13B to occur.

Figure 13C:
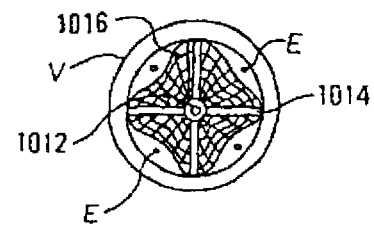

FIG. 13B depicts the situation that may obtain where the clinician overestimates the diameter of the vessel V, and selects filter 1010 having a deployed diameter larger than the nominal vessel diameter. As illustrated in FIG. 13C, because struts 1014 contact the interior surface of the vessel before becoming fully deployed, filter mesh 1016 may be incompletely brought into apposition with the vessel wall around its circumference. Consequently, as depicted in FIG. 13C, folds may occur in filter mesh 1016 that permit emboli E to once again bypass the filter, providing inadequate protection against embolization.

Figure 14:
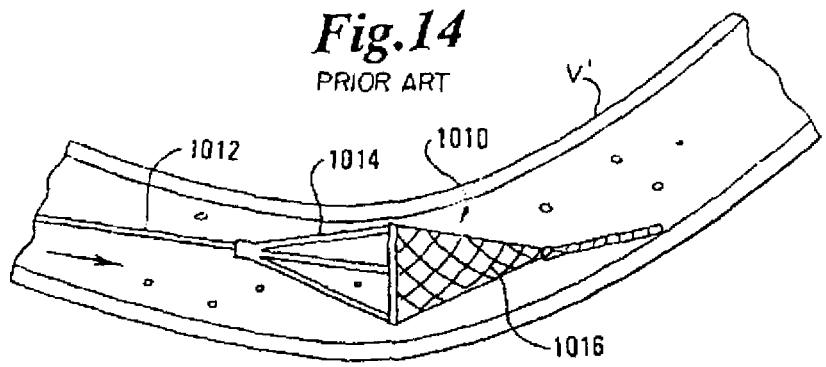
FIG. 14 is a side view of the vascular filter of FIG. 13 shown deployed in a tortuous vessel, where the stiffness of the guidewire causes the filter to partially collapse.

Referring now to FIG. 14, an alternative drawback of the previously known vascular filters is described, which drawback is common to both umbrella-type and single fixed hoop type disclosed in the aforementioned International Publication WO 98/39053. This problem is manifests where vascular filter 1010 is inserted into tortuous anatomy, and in particular, where it is necessary to place the filter in or near curved vessel V', such as in smaller coronary arteries and the renal arteries.

As depicted in FIG. 14, guidewire 1012 on which vascular filter 1010 is disposed spans the bend in vessel V'. Due to the stiffness of guidewire 1012 relative to strut 1014 of filter 1010, when inserted in vessel bend having a small radius of curvature, strut 1014 may become compressed against the inner bend surface of vessel V'. This load may in turn prevent filter 1010 from fully opening (or partially collapse the effected strut), permitting emboli to bypass the filter at the outer side of the bend.

Figure 15:
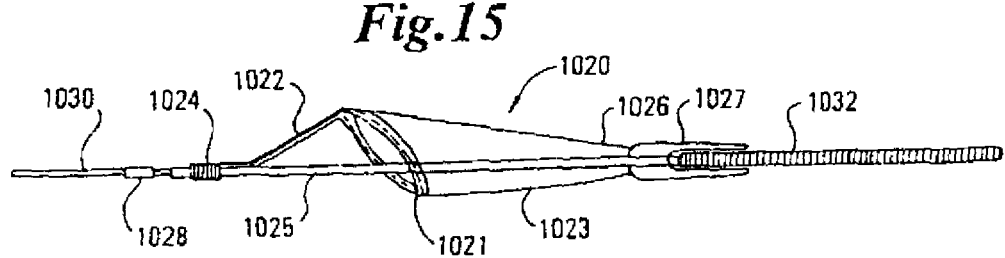
FIG. 15 is an side view of a vascular filter constructed in accordance with the principles of the present invention.

Referring now to FIG. 15, illustrative vascular filter 1020 of the present invention is described. Filter 1020 solves the above-described disadvantages by providing a filter that is expected to maintain apposition to a vessel wall even when used in tortuous vessels, vessels of uncertain size and those subject to localized temporal swelling caused by pressure pulsations.

Filter 1020 preferably includes self-expanding support hoop 1021 mounted on suspension strut 1022, and supports blood permeable sac 1023. Blood permeable sac comprises a biocompatible polymeric material having a multiplicity pores. Suspension strut 1022 is affixed at proximal end 1024 to tube 1025. Distal end 1026 of blood permeable sac 1023 is illustratively mounted to nose cone 1027, which is in turn mounted to tube 1025. Filter 1020 is mounted on guidewire 1030 between proximal stop 1028 and enlarged floppy tip 1032 of the guidewire, which functions as a distal stop. Tube 1025 permits guidewire 1030 to rotate independently of filter 1020, thereby permitting the floppy tip 1032 of guidewire to be directed within the vessel without causing the blood permeable sac to become wrapped around guidewire 1030.

Figure 16A:
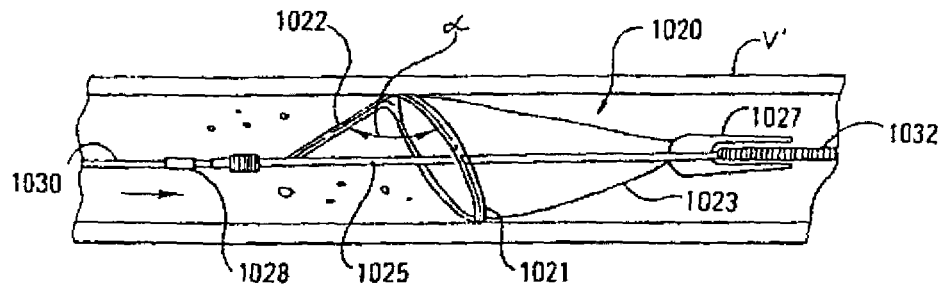
FIGS. 16A-16C are, respectively, side views of the vascular filter of FIG. 15 shown deployed in straight lengths of vessel of different diameters and in a tortuous vessel.
Figure 16B:
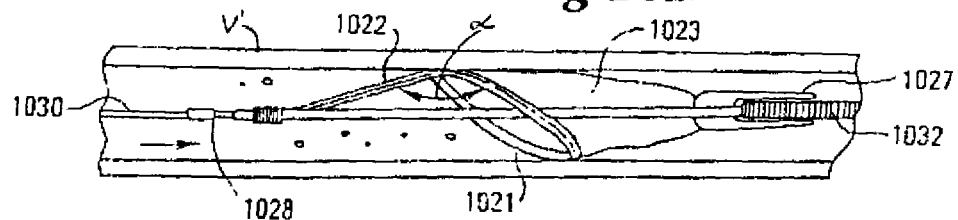
Figure 16C:
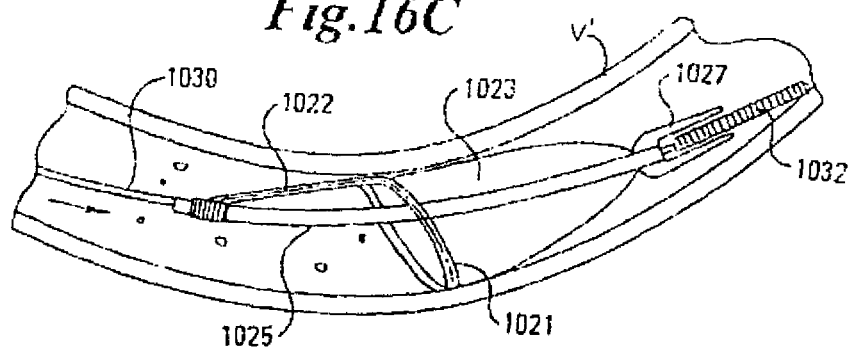

In accordance with the principles of the present invention, suspension strut 1022 positions support hoop 1021 approximately concentric to tube 1025 when disposed in a substantially straight length of vessel, as depicted in FIG. 16A, but permits the support hoop to become eccentrically displaced relative to support tube 1025 when the filter is deployed in a curved vessel, as depicted in FIG. 16C. Thus, unlike the case described above with respect to FIG. 14, the relative differences in stiffness between guidewire 1030 and suspension strut 1022 facilitate, rather than impede, proper deployment of the filter 1020 by permitting support hoop 1022 to become eccentrically displaced relative to guidewire 1030.

Referring now to FIGS. 16A and 16B, a principle advantage of the vascular filter of the present invention is described. As depicted in FIG. 16A, support hoop 1021 is disposed obliquely, rather than radially, relative to the longitudinal axis of the vessel. Importantly, this arrangement permits support hoop 1021 to be properly used in a variety of vessel sizes.

In larger diameter vessels, as depicted in FIG. 16A, angle .alpha. formed between suspension strut 1022 and support hoop becomes less oblique, and the support hoop less elongated (more nearly perpendicular to the vessel axis). By comparison, in the smaller diameter vessel depicted in FIG. 16B, angle .alpha. becomes more oblique, and the support hoop becomes more elongated and more closely parallel to the axis of the vessel. Filter 1020 has been observed to retain adequate engagement with the vessel wall around the filter circumference over a wide range of vessel sizes. Accordingly, filter 1020 may properly be used in a much wider range of vessel sizes than an umbrella-type filters, while providing superior apposition to the vessel walls. Thus, for example, a filter having a nominal diameter of 6 mm may be used in vessels having diameters between about 2.5 and 6.0 mm.

Figure 17:
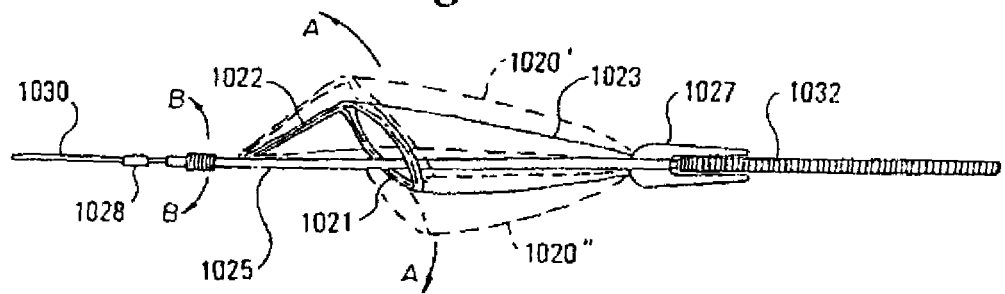
FIG. 17 is a side view illustrating that the suspension arrangement of the present invention permits torsional and lateral movement of the guide wire without displacing the support hoop or filter sac.

Referring now to FIGS. 16C and 17, the use of single flexible suspension strut 1022 permits the vascular filter to achieve good apposition to the vessel wall even in curved vessels, such as vessel V'. As shown in FIG. 17, vascular filter 1020 is capable of a wide range of eccentric lateral displacements in the direction shown by arrows A (indicated by dotted lines 1020' and 1020"). In addition, tube 1025 permits guidewire 1030 to rotate freely within the filter (shown by arrows B) without causing blood permeable sac 1023 to become wrapped around the guidewire. In addition, suspension strut 1022 absorbs minor longitudinal movements of guidewire 1030, without causing the support hoop 1021 to lose apposition to the vessel wall. Thus, transmission of minor longitudinal movements to the filter, e.g., associated with catheter exchange, are mitigated.

Figure 18A:
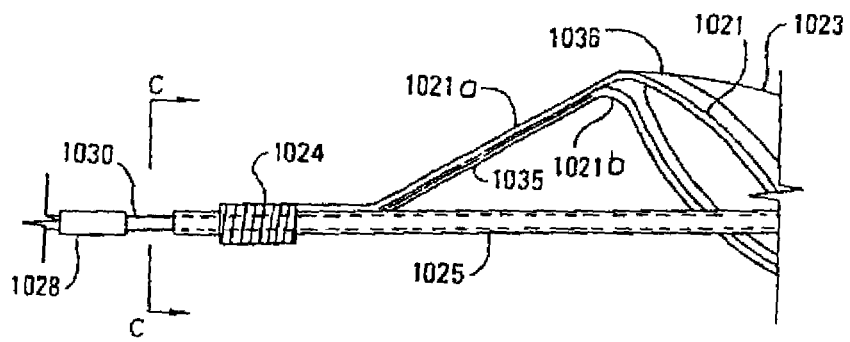
Figure 18B:
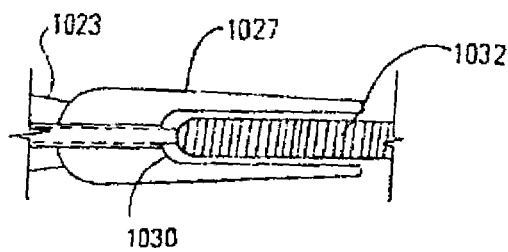
Figure 18C:
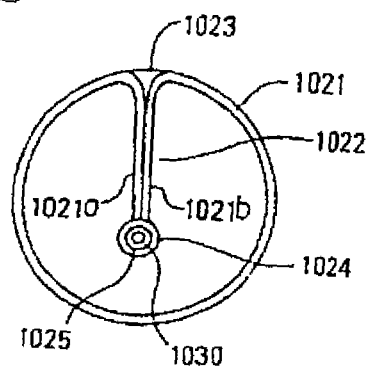

Referring now to FIGS. 18A to 18C, construction details of a preferred illustrative embodiment of the present invention are described. In FIG. 18A, detail of a preferred embodiment of support hoop 1021 and suspension strut 1022 are described. Suspension strut 1022 preferably is formed from proximally extending portions 1021a and 1021b of support hoop 1021, and may also include additional support member 1035 welded or bonded to portions 1021a and 1021b. Proximal portions 1021a and 1021b are attached at end 1024 to tube 1025, for example, by wrapping, welding, crimping or other suitable bonding method. Stop 1028 may comprise a weld bead, length of shrink tube, step in guidewire 1030, or similar structure that limits proximal movement of tube 1025 over guidewire 1030.

Support hoop 1021 comprises a hoop having a circular or rectangular cross-section that is formed of a super-elastic material, such as a nickel-titanium alloy ("nitinol"). During deployment and retrieval of vascular filter 1020, support hoop 1021 preferably folds in half and collapses to fit within the guidewire lumen of a standard balloon catheter, alternatively, a separate retrieval sheath may be employed. When vascular device 1020 is in a deployed state, as depicted in FIG. 15, support hoop 1021 resumes its pre-formed shape. Support hoop 1021 preferably comprises nitinol wire, although it may also be formed from a multi-strand nitinol cable, a spring tempered stainless steel, or other super-elastic material.

Support hoop 1021 optionally may include any of the articulation regions described in commonly owned U.S. Pat. No. 6,129,739, which is incorporated herein by reference. Thus, for example, support hoop may comprise a wire of uniform thickness, a wire having one or more reduced thickness regions, a wire having a gradual taper from its proximal ends towards its mid-point, or a pair of spines spanned by a polymer bridge or bridged by the overlapping seam of blood permeable sac 1023, as described in the above-incorporated patent.

Sac 1023 preferably is constructed of a thin, flexible biocompatible material, and is bonded to support hoop 1021 by seam 1036, or other suitable means described in the above-incorporated patent. Suitable materials for use in constructing sac 1023 include polyethylene, polypropylene, polyurethane, polyester, polyethylene tetraphlalate, nylon, polytetra-fluoroethylene, or combinations thereof. The sac material preferably is sufficiently thin that the sac is non-thrombogenic, and includes openings or pores that permit blood cells to pass through the sac substantially unhindered, while capturing any larger emboli, thrombus, or foreign bodies that may be released during a procedure, such as angioplasty or stent placement.

Advantageously, the number and distribution of pores may be tailored to the specification application of the vascular filter. Thus, for example, where the filter is to be used in conjunction with angioplasty of saphenous vein grafts, where large quantities of friable plaque are expected to be liberated, larger pores my be used to permit smaller particles to pass through the filter. In this case, it may be more desirable to permit small particles to pass through sac 1023, rather than clog the pores interrupt blood flow. By a comparison, smaller pores may be used in filters intended for carotid angioplasty applications, because less material is expected to be liberated and there may be a premium on preventing even small particle from reaching the brain.

In one preferred embodiment, sac 1023 has openings or pores in a range of about 20 to 400 microns in diameter, and more preferably, about approximately 80 microns. These pore sizes permit blood cells (which have a diameter of approximately 5 or 40 microns) to easily pass through the sac, while capturing thrombus or emboli. Other pore numbers and sizes may be empirically selected with regard to the potential trade-offs in efficacy, ease of use, and other related factors that will be apparent to one of skill in the art.

Additionally, the filter membrane may be coated with a lubricious coating that incorporates anti-thrombogenic agents, such as heparin. The lubricious coating, such as a hydrophobic or hydrophilic thin layer, however, should not occlude pores of the filter sac. Advantageously, such a lubricious coating may decrease friction between the blood permeable sac and the delivery sheath to enable a lower delivery profile for the vascular filter. The anti-thrombogenic agents also will reduce the amount of clot that forms on the filter membrane.

In a preferred method of manufacture, the pores in blood permeable sac 1023 are formed using a laser drilling process. In this process a thin sheet of the flexible biocompatible material is first thermoformed to create sac 1023, for example, by stretching the sheet over a mandrel, by dip forming, or by blow molding. Sac 1023 may alternatively be fabricated from an extruded tube of the biocompatible material. A flat metal mask, having holes approximately the size of the desired pores is then used to shield the sac, and a laser having a beam diameter equal to or greater than the diameter of the material illuminates the mask. Rays of the laser beam thereby pass through the holes in the mask and strike the material to form the pores.

Laser drilling also may be accomplished using a laser having a beam diameter approximately the size of the desired pores, in which case the pores are drilled individually. Sac 1023 alternatively may comprise a woven material, for example, formed from the above-mentioned polymers, having a pore diameter determined as a function of the pattern and tightness of the weave.

Referring now to FIG. 18B, nose cone 1027 preferably is disposed from a distal end of tube 1025, and includes an internal bore that accepts a proximal portion of floppy tip 1032. This configuration shortens the overall length of floppy tip 1032 extending beyond the distal end of sac 1023, and may be especially desirable for filters intended in short or very tortuous vessels, such as the renal arteries. While in the embodiment of FIGS. 15-18, blood permeable sac is attached at its distal end to nose cone 1027, it is to be understood that the distal end of sac 1023 alternatively may be affixed to tube 1025.

FIG. 18C provides an end view of vascular filter 1020 taken along view line C-C of FIG. 18A. Suspension strut 1022 includes proximally extending portions 1021a and 1021b of support hoop 1021, and additional support member 1035 is obscured from view. Portions 1021a and 1021b are wrapped around tube 1025 to from attachment point 1024. When viewed along line C-C, support hoop 1021 (and deployed in a vessel), support hoop 1021 and sac 1023 conform to the perimeter of the vessel, and appear circular.

In one preferred embodiment of vascular filter 1020 of the present invention, filter 1020 easily fits within a delivery sheath having an inner diameter of 0.033", and, more preferably, may be used with a delivery sheath having an inner diameter of about 0.026". The deployed diameter of support hoop 1021 preferably is approximately 7 mm, while guide wire 1030 preferably has a diameter of 0.014".

Support hoop 1021 preferably is constructed of 0.0035"nitinol wire tapered (by a grinding, chemical etching, or electroless polishing process) to 0.002" at a point on the support hoop opposite to the point where the support hoop joins suspension strut 1022. Support hoop 1021 also may include radiopaque features, such as gold or platinum bands (not shown), spaced at intervals around the circumference of support hoop 1021, or a flat or round coil of radiopaque material wrapped around the support hoop, or a gold plated coating.

Advantageously, the compliant design of vascular filter 1020 permits the filter to be contracted to its delivery state within the guide wire lumen of conventional previously known interventional devices. Accordingly, unlike previously known vascular filters, which typically require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

It is contemplated that in operation, the vascular filter of the present invention will be deployed in a vessel using a delivery sheath, such as described hereinafter. The guidewire to which the vascular filter is attached then is used to insert an interventional device, e.g., an angioplasty catheter, atherectomy device or stent delivery system, to perform the desired diagnostic or therapeutic procedure. Upon completion of the procedure, the interventional device is advanced to capture the filter, and the vascular filter and interventional device are withdrawn together.

Alternatively, the interventional device may be held stationary, and the guidewire retracted proximally to pull the vascular filter into the guidewire lumen of the interventional device. This latter method of retrieving the vascular filter may be particularly advantageous, because as the filter is dragged along the vessel wall (or through the interior of a stent, if deployed), additional emboli material may be collected from the vessel wall. Accordingly, emboli that might not be liberated until full flow is restored to the vessel may be collected in this manner prior to closure and withdrawal of the vascular filter.

Figure 19A:
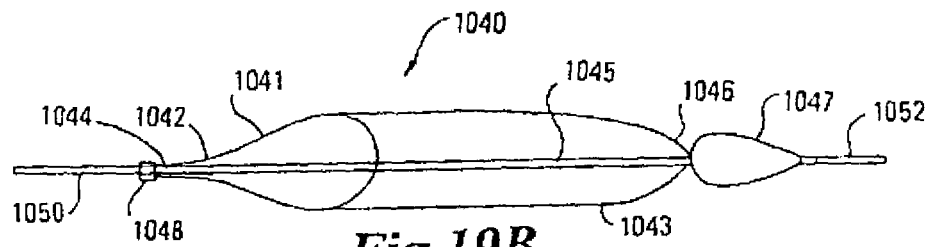
FIGS. 19A-19C are side, top and end views of an alternative embodiment of the vascular filter of the present invention.
Figure 19B:
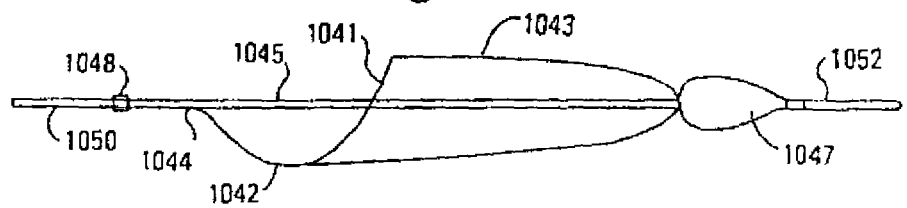
Figure 19C:
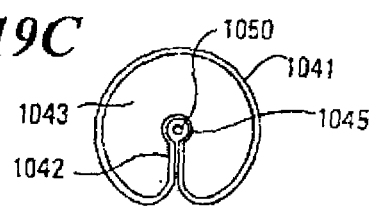

Referring now to FIGS. 19A-19C, an alternative embodiment of the vascular filter of the present invention is described. Vascular filter 1040 is similar in construction to filter 1020 to FIGS. 15-18, and includes support hoop 1041, suspension strut 1042, sac 1043, fixation point 1044, tube 1045 and nose cone 1047. Tube 1045 is mounted for rotation on guidewire 1050 between proximal stop 1048 and floppy tip 1052. Filter 1040 preferably is constructed in the manner and with the materials described hereinabove.

Filter 1040 differs from filter 1020, described hereinabove, in that suspension strut 1042 is gradually curved, and the distal end 1046 of blood permeable sac 1043 is affixed to tube 1025, rather than nose cone 1046. As for the embodiment of FIGS. 15-18, support hoop is elliptical when viewed in profile, but includes a single multi-strand suspension strut 1042 that permits the filter sac to become eccentrically displaced from guidewire 1050 without losing proper apposition to the vessel wall.

Figure 20A:
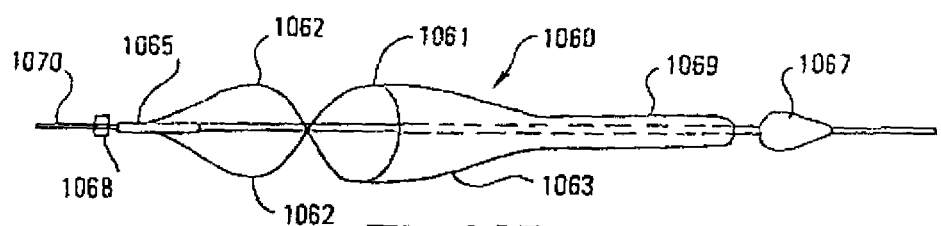
FIGS. 20A and 20B are side and top views of another alternative embodiment of the present invention.
Figure 20B:
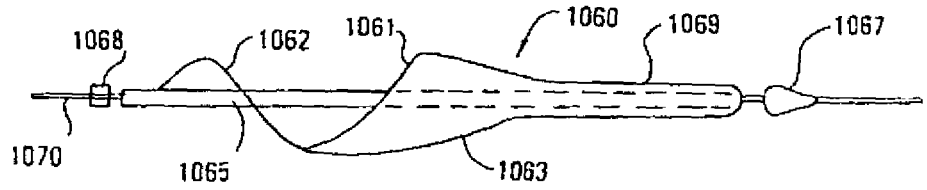

With respect to FIGS. 20A and 20B, another alternative embodiment of the vascular filter of the present invention is described. Vascular filter 1060, shown in the deployed state, comprises support hoop 1061 coupled to multi-turn helical suspension struts 1062. Suspension struts 1062 are coupled to tube 1065, which is captured on guidewire 1070 between proximal stop 1068 and nose cone 1067. Nose cone 1067 is affixed to guidewire 1070 distal of tube 1065. The proximal end of blood permeable sac 1063 is affixed to support hoop 1061, while the distal end is affixed directly to tube 1065. Suspension strut 1062 includes one or more side turns 1069 that join support hoop 1061. Blood permeable sac 1063 includes tapered distal portion which is expected to reduce the risk of bunching during retrieval.

In accordance with this aspect of the present invention, vascular filter 1060 may be contracted to small profile delivery state. When deployed from a delivery catheter, side turns 1069 expand into contact with the walls of the vessel proximal to the location at which support hoop 1061 contacts the vessel wall. Side turns 1069 of suspension struts 1062 are expected to stabilize support hoop 1061 and sac 1063 when vascular filter 1060 is deployed within a blood vessel. In addition, side turns 1069 are expected to facilitate eccentric displacement of support hoop 1061 and sac 1063 relative to the longitudinal axis of a vessel. Accordingly, side turns 1069 of suspension struts 1062 are expected to enhance apposition of the filter against the vessel wall, and thus further enhance the safety and reliability of the device.

Figure 21:
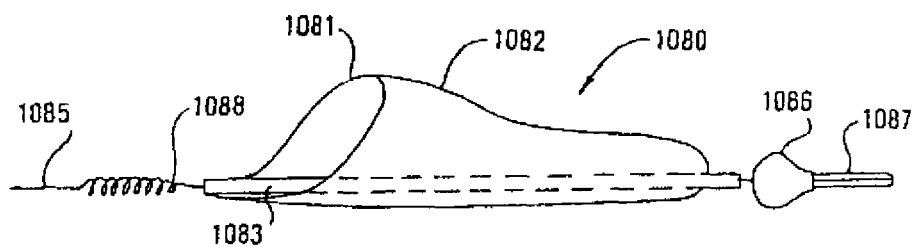
FIG. 21 is a side view of a further alternative embodiment of a vascular filter of the present invention in a deployed state.
Figure 22:
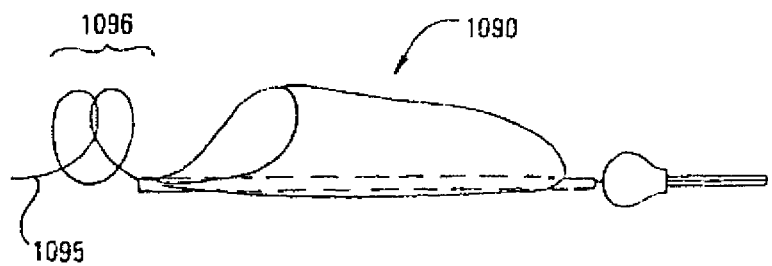
FIG. 22 is a side view of a yet another alternative embodiment of a vascular filter of the present invention in a deployed state.

Referring now to FIGS. 21 and 22, additional alternative embodiments of the vascular filter of the present invention are described. In FIG. 21, vascular filter 1080 comprises support hoop 1081 and tapered blood permeable sac 1082 mounted on tube 1083. Support hoop 1081 is coupled directly to the proximal end of tube 1083. Filter 1080 is captured on guidewire 1085 between nose cone 1086, which is affixed to guidewire 1085 just proximal of floppy tip 1087, and proximal stop 1088.

In accordance with the principles of the present invention, guide wire 1085 includes articulation region 1089 comprising a series of small diameter coil turns. Articulation region 1089 acts as a bend point in the guide wire, thereby permitting better conformance of the guidewire to tortuous anatomy and improved capture efficiency in tortuous vessels, such as illustrated in FIG. 14. Articulation region 1089 therefore provides an alternative configuration for permitting the vascular filter to become displaced eccentrically displaced relative to the axis of guidewire 1085.

FIG. 22 depicts an alternative configuration of the vascular filter of FIG. 21, in which filter 1090 is essentially constructed in the same manner as filter 1080. In this embodiment, however, guidewire 1095 includes an articulation region 1096 that comprises two or more large diameter coils. In addition to providing region that permits articulation of the filter relative to the axis of guidewire 1095, the large diameter coils of the articulation region 1096 also may assist in stabilizing the filter within the vessel after deployment.

Figure 23:
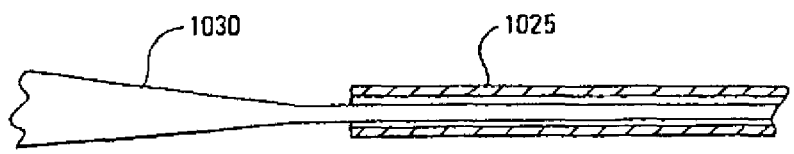
FIG. 23 is detailed view of a tapered guide wire and support tube arrangement suitable for use in the present invention.

Referring now to FIG. 23, an additional feature that may be advantageously incorporated in the embodiments of the vascular filters of the present invention is described. FIG. 23 depicts an alternative configuration for the junction between a guidewire and the tube on which the filter is mounted. For example, the guidewire in FIG. 23 may be guidewire 1030 of the embodiment of FIG. 15, and the tube may represent tube 1025 of that embodiment. In accordance with this aspect of the present invention, guidewire 1030 is tapered as shown (or includes a step, not shown) to accept tube 1025. Consequently, the outer diameter of tube 1025 may be made approximately the same as the guidewire thickness itself.

Because the delivery profile of the vascular filter is determined in part by the cumulative thicknesses of the components that lie adjacent to one another in the delivery sheath, use of a tapered or stepped distal region of the guidewire to accept tube 1025 may enable the manufacture of significantly smaller profile devices than heretofore available. For example, in an umbrella-type filter, the delivery profile is limited by the need to have multiple struts disposed about the guidewire, and accounts for the difficulty that has been encountered in the field in constructing such filters at small delivery profiles. By comparison, a filter of the type described hereinabove when collapsed to its delivery profiled, and using the feature illustrated in FIG. 23, need not be much larger than diameter of the guidewire itself.

Figure 24A:
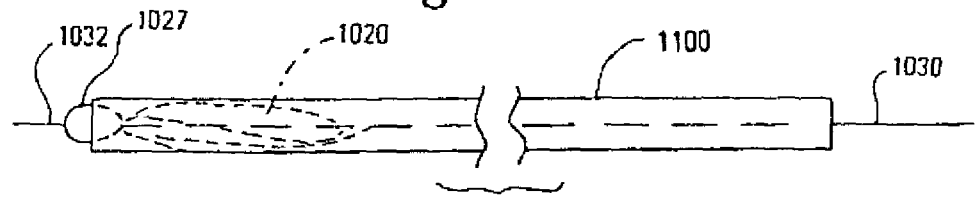
FIGS. 24A-24C are side views illustrating deployment of the vascular filter of the present invention using a single use splittable delivery sheath.
Figure 24B:
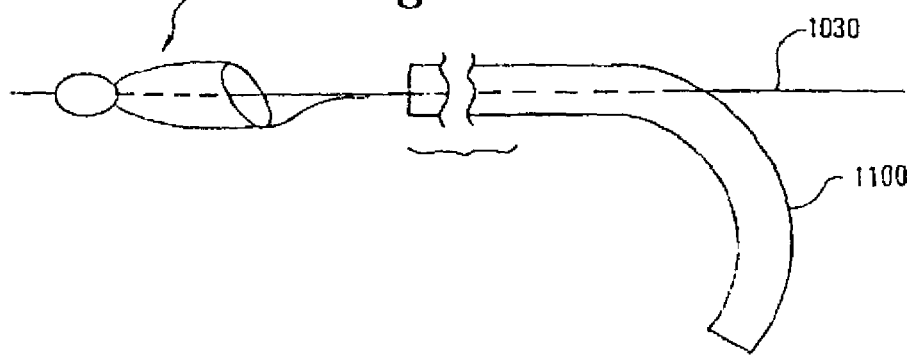
Figure 24C:
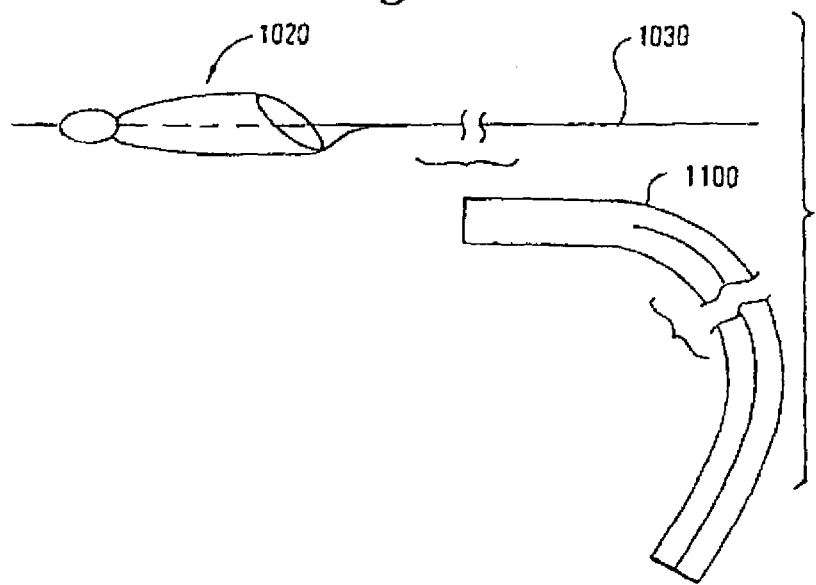

Referring now to FIGS. 24A-24C, a single-use delivery sheath suitable for use with the vascular filter of the present invention is described. In accordance with this aspect of the present invention, guidewire 1030 may be of a length suitable for use with rapid-exchange interventional devices. Vascular filter 1020 is disposed in delivery sheath 1100 in its contracted configuration, with the proximal end of guidewire 1030 extending from the proximal end of sheath 1100 and nose cone 1027 and floppy tip 1032 extending from the distal end of the sheath, as shown in FIG. 24A. Delivery sheath 1100 preferably comprises a soft, flexible biocompatible material, such as polyethylene or other materials typically used in catheter construction.

In accordance with known techniques, the distal region of guidewire 1030 and vascular filter are percutaneously and transluminally inserted into a patient until the vascular filter is at a desired deployment site, as determined, for example, by fluoroscopy. Delivery sheath 1100 is then split, either using a suitable cutting device or along a perforation seam, and retracted proximally to deploy vascular filter 1020 within the vessel, as shown in FIG. 24B.

Delivery sheath 1100 then is retracted proximally, with the clinician holding the proximal end of guidewire 1030 in one hand, and splitting the delivery sheath along the perforation line (or with a cutting tool, not shown) until proximal end of the delivery sheath is withdrawn from the patient. At this point, the clinician may then slip the proximal end of the guidewire through the remaining unsplit portion of the delivery sheath, thereby fully removing the delivery sheath from guidewire 1030, as shown in FIG. 24C.

Guidewire 1030 may thereafter be used in a conventional rapid exchange manner for passing interventional devices, such as atherectomy devices, angioplasty device, and stent delivery systems, to desired locations in the vessel proximal to the location of vascular filter 1020. Once the intended diagnostic or therapeutic treatment is performed, guidewire 1030 is withdrawn proximally until the support hoop is drawn within the guidewire lumen of the interventional device, thereby closing the mouth of the filter and preventing emboli collected during the procedure from escaping into the patient's blood stream.

Advantageously, the vascular filter system, when used with delivery sheath 1100, eliminates the need for a separate catheter exchange to insert a retrieval catheter to recover the filter. In addition, single-use delivery sheath 1100 will discourage off-label repeat use of the vascular filter such as may occur if a separate delivery and retrieval sheath were used, because the delivery sheath is nonreusable once the filter has been deployed once. Further still, because delivery sheath 1100 need not be capable of transmitting pushing forces, the walls of the sheath may be made very thin.

Figure 25A:
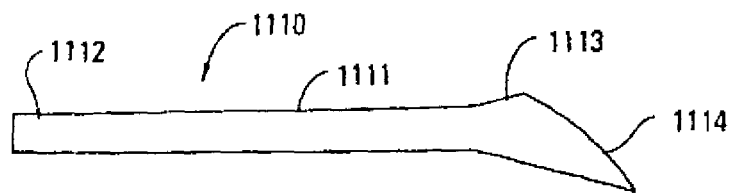
FIGS. 25A and 25B are, respectively, side and top views of an introducer sheath suitable for use with the vascular filter of the present invention.
Figure 25B:
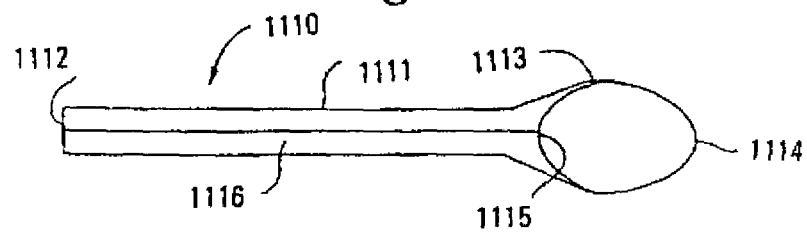

Referring now to FIGS. 25 and 26, introducer sheath 1110 and methods of using that sheath in conjunction with vascular filter 1020 and delivery sheath 1100 of the present invention are described. Introducer sheath 1110 is designed to pass floppy tip 1032 of guidewire 1030 through the rotating hemostatic valve of a guide catheter without kinking or tangling the floppy tip in the valve. Introducer sheath 1110 comprises tubular body 1111 having distal end 1112, funnel-shaped proximal end 1113, pull tab 1114, central lumen 1115 and full-length slit 1116, and preferably comprises polyethylene, nylon or similar material, having sufficient rigidity to be pushed through a rotating hemostatic valve.

Figure 26A:
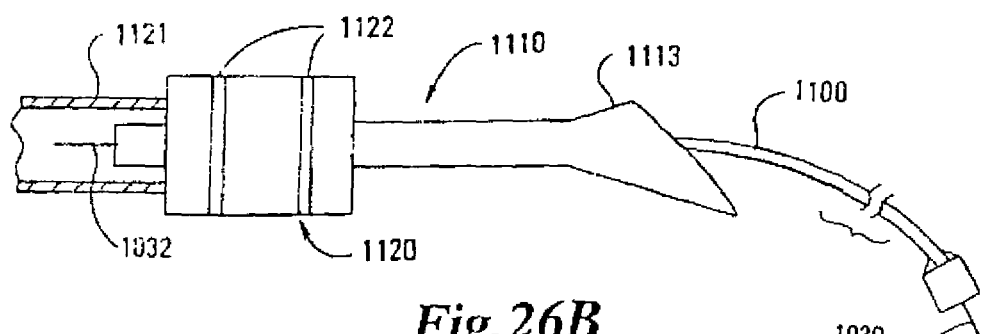
FIGS. 26A and 26B are side views, partially in section, illustrating use of the introducer sheath of FIG. 25 in crossing a rotating hemostatic valve.
Figure 26B:
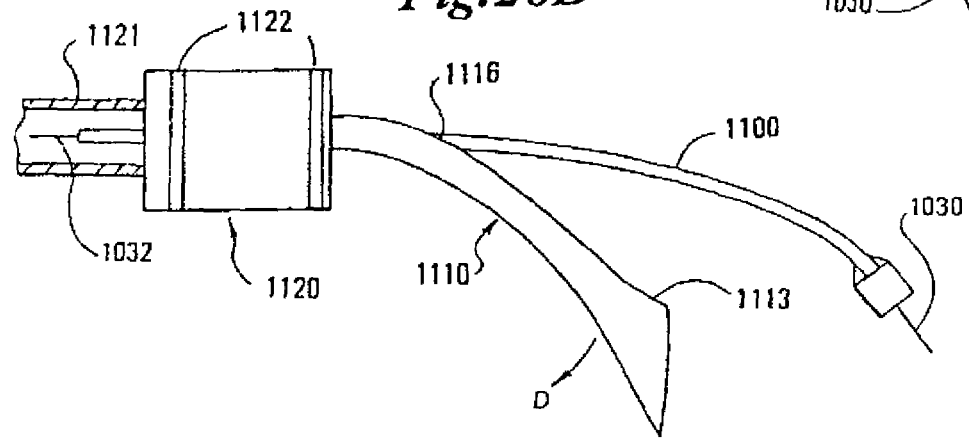

In a preferred method of use, illustrated in FIGS. 26A and 26B, introducer sheath 1110 is advanced through rotating hemostatic valve 1120 of guide catheter 1121. As will of course be understood by one of skill in the art, guide catheter 1121 may be a conventional multi-port guide catheter and includes a membrane that is selectively opened and sealed by rotating nuts 1122 of the valve. Delivery sheath 1100, which encloses vascular filter 1020 and guidewire 1030, then is inserted into funnel-shaped end 1113 of the introducer sheath, and advanced to a location at which floppy tip 1032 extends into guide catheter 1121 distal to valve 1120, as depicted in FIG. 26A.

Referring to FIG. 26B, pull tab 1114 of introducer sheath 1110 is pulled downward in the direction shown by arrow D so that delivery sheath 1100 passes through slit 1116 of the introducer sheath. Introducer sheath 1110 is retracted proximally and peeled away from delivery sheath 1100 as shown in FIG. 26B until the introducer sheath is entirely removed. Delivery sheath 1100, vascular filter 1020 and guidewire 1030 then are advanced to the desired location in the vessel, and delivery sheath 1100 is removed to deploy the vascular filter as described hereinabove with respect to FIGS. 24A-24C.

Advantageously, introducer sheath 1110 permits the floppy tip 1032 of guidewire 1030 to be easily inserted through rotating hemostatic valve 1120 of guide catheter 1120. The peel-away operation of introducer sheath 1110 facilitates rapid insertion of the vascular filter and guidewire into the guide catheter with little effort. In addition, slit 1116 of introducer sheath 1110 prevents destruction of the sheath after the single use, thus enabling the introducer sheath to be used to reintroduce the vascular filter in the same procedure. This may occur, for example, where the clinician begins inserting the vascular filter, but then needs to remove the filter and redirect the floppy tip during the same procedure.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus suitable for filtering emboli, comprising:
    a guide wire having a proximal region, a distal region, and a floppy distal tip;
    a filter attached to the distal region of the guide wire, the filter having a contracted configuration and an expanded configuration;
    wherein the filter includes a support hoop having an articulation region and a blood permeable sac forming a proximal-facing mouth; and
    a sheath comprising:
        a lumen extending therethrough; and
        a distal end having a locking wedge;
    wherein the filter is disposed within the lumen of the sheath in the contracted configuration.

2. The apparatus of claim 1, wherein the filter further comprises a spinner tube slidably and rotatably disposed about the guide wire.

3. The apparatus of claim 2, wherein the blood permeable sac is attached along its length to the spinner tube.

4. The apparatus of claim 2, wherein the spinner tube further comprises a nose cone.

5. The apparatus of claim 1, the support hoop further including a first curved region and a second curved region;
    wherein the articulation region is disposed between the first curved region and the second curved region.

6. The apparatus of claim 5, wherein first curved region and the second curved region articulate at the articulation region and the support hoop folds to a predetermined shape in the contracted configuration.

7. The apparatus of claim 5, wherein the first curved region opposes the second curved region about the guide wire.

8. The apparatus of claim 7, wherein retracting the sheath relative to the guide wire deploys the filter from the distal end of the sheath.

9. The apparatus of claim 5, wherein the wedge of the locking distal end of the sheath is configured to engage the first curved region and the second curved region when the filter is in the expanded configuration, thereby inhibiting articulation of the support hoop and maintaining the support hoop in the expanded configuration.

10. The apparatus of claim 1, wherein the support hoop tapers to a minimum thickness at the articulation region.

11. The apparatus of claim 1, wherein the support hoop comprises a super elastic material.

12. Apparatus suitable for filtering emboli, comprising:
    an elongated member having a distal region having a longitudinal axis;
    a filter frame disposed on the elongated member, the filter frame having a hoop portion at least partially forming a filter mouth and a curved strut portion extending longitudinally in a proximal direction,
    wherein the hoop portion includes a reduced thickness articulation region; and
    a polymeric blood permeable sac affixed to the hoop portion so that the filter mouth is a proximally facing mouth of the blood permeable sac.

13. The apparatus of claim 12, wherein the curved strut portion includes a first strut curving in a first direction and a second strut curving in a second direction opposite the first direction.

14. The apparatus of claim 12, wherein the curved strut portion is a multi-turn helical suspension strut.

15. The apparatus of claim 12, wherein the apparatus includes a rotation tube mounted between a proximal stop and a distal floppy tip that acts as a stop,
    wherein the sac is disposed on the rotation tube.

16. The apparatus of claim 15, further including a nose cone distal of the rotation tube.

17. The apparatus of claim 12, further comprising a second filter frame slideably disposed on the elongated member, the second filter frame having a hoop portion at least partially forming a filter mouth; and
    a polymeric blood permeable sac affixed to the hoop portion.

18. Apparatus suitable for filtering emboli, comprising:
    a guidewire having a proximal region and a distal region;
    a first support hoop attached to the distal region of the guidewire, the first support hoop having a contracted configuration and an expanded configuration,
    wherein the first support hoop forms a mouth for a first blood permeable sac attached thereto;
    a second support hoop slideably attached to the guidewire, the second support hoop having a contracted configuration and an expanded configuration,
    wherein the second support hoop forms a mouth for a second blood permeable sac attached thereto;
    the lumen of the sheath adapted to contain the first support hoop in the contracted configuration as well as the first blood permeable sac; and
    a second sheath comprising a lumen adapted to contain the second support hoop in the contracted configuration as well as the second blood permeable sac,
    wherein the second support hoop and second blood permeable sac are adapted to be advanced and retracted relative to the guidewire independently of the first support hoop and first blood permeable sac.

19. The apparatus of claim 18, wherein the first support hoop includes first and second curved regions and a reduced thickness articulation region disposed between the first and second curved regions.

20. The apparatus of claim 18, wherein the second support hoop includes first and second curved regions and a reduced thickness articulation region disposed between the first and second curved regions.

21. The apparatus of claim 18, wherein the first sheath is adapted to be removed from the first support hoop and first blood permeable sac independently of the removal of the second support hoop and second blood permeable sac from the second sheath.

22. The apparatus of claim 18, wherein the first support hoop is adapted to expand from the contracted configuration to the expanded configuration upon removal of the first sheath therefrom.

23. The apparatus of claim 18, wherein the second support hoop is adapted to expand from the contracted configuration to the expanded configuration upon removal of the second sheath therefrom.

24. The apparatus of claim 18, wherein the first support hoop is attached to the distal region of the guidewire by a support tube adapted to slide and rotate about the guidewire.

\* \* \* \* \*